United States Patent
Bae et al.

(10) Patent No.: US 6,562,362 B1
(45) Date of Patent: May 13, 2003

(54) LIQUEFIED EMBOLIC MATERIALS CAPABLE OF SOL-GEL PHASE TRANSITION AND THEIR USE

(75) Inventors: You Han Bae, Kwangju Kwangyeok-si (KR); Kun Na, Kwangju Kwangyeok-si (KR); Seong Il Kang, Kwangju Kwangyeok-si (KR); Jin Woo Yi, Kwangju Kwangyeok-si (KR); Moon Hee Han, Seoul (KR)

(73) Assignee: Kwangju Institute of Science and Technology, Kwangju Kwangyeoki-si (KR)

( * ) Notice: Subject to any disclaimer, the term of this patent is extended or adjusted under 35 U.S.C. 154(b) by 67 days.

(21) Appl. No.: 09/706,870

(22) Filed: Nov. 7, 2000

(30) Foreign Application Priority Data

Sep. 21, 2000 (KR) ......................................... 2000-55585

(51) Int. Cl.⁷ .................................................. A61F 2/00
(52) U.S. Cl. ........................ 424/425; 424/422; 424/423; 424/424; 424/426
(58) Field of Search ................................. 424/426, 422, 424/423, 425, 424; 528/373; 524/747

(56) References Cited

U.S. PATENT DOCUMENTS 6,103,865 A * 8/2000 Bae et al. .................... 528/373

6,238,688 B1 * 5/2001 Wu et al. .................... 424/426

OTHER PUBLICATIONS

Kaetsu, et al. Controlled Release by Thermorespnsive Sol–gel Transition Systems, Proceedings of the International Symposium on Controlled Release of Bioactive Materials (1998), 25$^{th}$, 880–881 (abstract).*

Veron, et al. Thermoreversible copolymer gels for extracellular matrix, J Biomed Mater Res (2000) Jul; 51(1):69–79 (abstract).*

Bae et al. Extracellular matrix for a rechargeable cell delivery system, J Control Release Apr. 30, 1998; 53(1–3): 249–58 (abstract).*

* cited by examiner

Primary Examiner—Thurman K. Page
Assistant Examiner—Rachel M. Bennett
(74) Attorney, Agent, or Firm—Rosenberg, Klein & Lee

(57) ABSTRACT

Disclosed are liquefied embolic materials capable of sol-gel phase transition in response to in vivo conditions, including temperature, ionic strength, and pH, and their uses. The liquefied embolic materials are made of copolymers based on temperature-sensitive isopropylacrylamide and ionic strength- and/or pH-sensitive monomers. In addition to finding excellent applications in the embolotherapy, the embolic materials can be used as extracellular matrixes for cell culture and for drug-delivery systems for cancer therapy.

11 Claims, 1 Drawing Sheet

LIQUEFIED EMBOLIC MATERIALS CAPABLE OF SOL-GEL PHASE TRANSITION AND THEIR USE

BACKGROUND OF THE INVENTION

1. Field of the invention

The present invention relates to liquefied embolic materials capable of sol-gel phase transition in response to in vivo conditions, including temperature, ionic strength, and pH, and their uses. More particularly, the present invention relates to liquefied embolic materials made of copolymers which are based on temperature-sensitive isopropylacrylamide and ionic strength- and/or pH-sensitive monomers. Also, the present invention is concerned with pharmaceutically acceptable, embolic compositions comprising the embolic materials in liquid forms.

2. Description of the Prior Art

Embolotheraphy is a medical technique of closing dysfunctional blood vessels to normalize distorted blood flow or of obstructing the blood flow around lesions, especially cancers, to reduce sizes of the lesions (cancers), induce the withering of the disease entities to death, and simplify the operation for the removal of lesions with a minimal hemorrhage.

In order to embolize blood vessels, there have been developed a variety of embolic materials and devices, from among which the selection of appropriate ones is determined depending on the types, sizes and locations of target blood vessels. Generally, consisting of particulate synthetic polymers, human tissue fragments, or curable liquid materials, embolic materials are classified as "degradable" and non-degradable" depending on their biodegradability.

On the whole, a vascular embolic material must satisfy the following requirements: 1) that it completely embolize target blood vessels, 2) that it exhibit minimal toxicity with substantial absence of side effects to tissues around the locus where it is introduced, 3) that it cause minimal pain and be safe, 4) that it perform embolization with a high rate of success and prevent recurrence of blood flow, 5) that it allow convenience for the operation, 6) it be low in cost, and 7) it be applicable for blood vessels of various loci. Thus far, no vascular embolic materials have been reported which meet all the above requirements. For example, vascular embolic materials heretofore proposed are virtually impossible to apply for all types of embolization for various reasons, such as locations of blood vessels of interest, relevant organs, disease seriousness and so on.

For embolization, there have been developed a variety of types of means, including particulate materials and balloon devices. In recent times, liquid forms of embolic materials have been of special concern to those in the art for their ability to embolize fine blood vessels. Following are the materials suitable for use for this purpose.

Bucrylate (isobutyl-2 cyanoacrylate)

Representative of the embolic materials which can be used in a liquid form at present, bucrylate, widely known as an instantaneous adhesive, is polymerized to a polymer by anion polymerization mechanism in the presence of water. In the medial field, this material is also used as an adhesive for tissues. Because of its rapid polymerization rate, bucrylate may be used in combination with glacial acetic acid to control its reaction rate when being used for embolization. However, this material suffers from the disadvantages of demanding a highly skilled expert in its application for embolization, owing to its polymerization being very difficult to control, and the requirement for use of an injection catheter which is specially designed not to be clogged by the material. What is worse, bucrylate may cause cancers in the body. Thus, it is recommended to use this putative carcinogenic material only for patients who are in critical condition. In addition, the biomedical effects of its biodegradation procedure and products of decomposition are highly controversial.

Silicon

Silicon is injected, along with oligomers, crosslinking agents and catalysts, into blood vessels with the crosslinking rate being controlled by the mixture ratio of the components, as disclosed in U.S. Pat. No. No. 4,551,132. Advantages of the silicon material described in, this reference patent are its superb compatibility with blood without causing cancers. In addition, the silicon material is advantageous in that it is less toxic in vivo than other embolic materials and the length of time taken for coagulation in the blood vessel of a living body can be controlled within a wide range. However, the silicon material suffers from the drawback of being inconvenient for injection because of its high viscosity. Another drawback with the silicon material is that blood vessels, if small in diameter, cannot be selectively embolized by use of the silicon material.

Absolute Ethanol

Absolute ethanol damages endothelial cells of blood vessels and denaturates proteins of the tissues, giving rise to blood coagulation. With these advantages, this material is useful to embolize fine blood vessels. The use of absolute ethanol in embolization is usually accompanied by employing balloon catheters to prevent the backflow of enthanol. For this reason, absolute ethanol is difficult to apply for the embolization of cerebral vascular systems.

Thermosensitive Embolic Material

In recent times, there have been introduced thermosensitive polymers which are liquid at low temperatures but transform into solid forms at the body temperature. U.S. Pat. No. 5,525,334 discloses a method for vascular embolization of blood vessels, which takes advantage of this phase transition of such a thermosensitive polymer. In this method, an aqueous solution of a thermosensitive polymer is introduced into a blood vessel followed by in situ heating of the solution to cause coagulation. Because its phase transition is absolutely dependent on temperature, the material described in the reference patent, based fundamentally on isopropyl acrylamide, has the problem of clogging the catheter in use therewith as a result of the phase transition occurring within the catheter. Also, the thermosensitive embolic material cannot be transformed into a gel mass strong enough to withstand normal blood pressure, so that a complete vascular embolizing effect is not obtained.

Many other materials available for use in embolization have been developed. For example, U.S. Pat. No. 4,172,066 describes spheroidal microgels of a water-swollen or water-swellable, cross-linked polymer such as cross-linked polyacrylamide. In U.S. Pat. No. 4,358,355, there is described a polymeric material comprising acrylamide or derivatives thereof, acrylonitrile or derivatives thereof, acrylic acid and esters, or derivatives thereof, sulphonyl or phosphonyl derivatives, which can be used as components of gels. Another material is found in U.S. Pat. No. 4,732,930 which relates to an ionic gel formed by polymerization of isopropylacrylamide in the presence of an ion-containing monomer. This gel is capable of drastic volume change in response to external conditions. All of the gels described above, however, are problematic in that they cannot completely close blood vessels and may be leaked out of the blood vessels.

SUMMARY OF THE INVENTION

Therefore, it is an object of the present invention to overcome the above problems and disadvantages encountered in the prior art, such as inability to control the polymerization of monomers and to selectively embolize blood vessels of interest and clogging of injection catheters, and to provide a novel liquefied embolic material capable of sol-gel phase transition, which completely embolizes blood vessels of interest and prevents the recurrence of blood streaming in addition to being minimized in toxicity and side effects.

It is another object of the present invention to provide a pharmaceutical composition for embolizing blood vessels, which is based on the embolic material.

Because of its being converted to gel under a specific set of conditions defined by a temperature parameter, an ionic strength parameter and a pH parameter, the liquefied embolic material according to the present invention is free from clogging catheters by being gelled within catheters, unlike conventional materials sensitive only to temperature. Under the conditions which meet all the requirements for temperature, ionic strength and pH, the liquefied embolic material of the present invention is instantaneously converted into a solid form, thereby preventing itself from being released out of the lesion where it is injected.

In accordance with the present invention, the embolic material is a ready-polymerized polymeric mass which need not be further polymerized, so that polymerization of monomers does not occur within the human body. Additionally, no organic solvents are used upon the application of the embolic material; thus it avoids the side effects attributable to solvent leakage. Further, the embolic material can be applied to a broad spectrum of lesions, including solvent-sensitive loci.

Being non-degradable, the embolic material of the present invention can bring about the effect of preventing the recurrence of blood flow in the embolized blood vessel.

Constituting the embolic material of the present invention, synthetic copolymers can be made to have diverse molecular weights and viscosity properties by changing proportions of monomers and through different polymerization processes: embolic materials can be readily made suitable for use in the embolization of blood vessels of interest.

Over homopolymers consisting of, for example, isopropylacrylamide alone, the copolymers according to the present invention have the advantage in that they show high gel stability. When being used in combination with other particulate embolic materials, such as microspheres with a size of 0.1–100 μm, each consisting of natural (proteins, polysaccharides, etc.) or synthetic polymers (PVA, PEG-PLLA) capable of encapsulating drugs of interest, and natural polymers helpful in stabilizing the gel, such as hyaluronic acid, carboxylated curdlan, pullulant and alginic acid, the embolic material exhibits better gel stability than when being used alone.

Superiority of the embolic material of the present invention to conventional ones can be proven in the field of histoengineering, which is directed to manufacture of artificial organs. To manufacture an artificial organ, a great number of cells are required, which are usually obtained by a three-dimensional culture process in which cells are fixed onto a matrix and cultured to a desired number, followed by the separation of the cultured cells from the matrix through spontaneous decomposition or compulsory removal of the matrix. The polymer prepared according to the present invention is useful as such a matrix. For example, the matrix made of the polymer of the present invention is maintained in a gel phase under a cell culture condition, e. g. at 37° C. and returned to a sol phase when the temperature is lowered after completion of the culturing, segregating easily from the cells. On the other hand, the conventional polymer consisting mainly of isopropylamine cannot be converted at 37° C. into gel hard enough to be used as a matrix for cell culture.

Also, the present invention finds an excellent application in the drug-delivery system for cancer therapy. As soon as they are administered in a conventional cancer therapy, anti-cancer drugs are diffused not only to perform their therapeutic functions against cancers, but also to cause various side-effects in normal cells. In contrast, as soon as it is administered into a cancer locus, in combination with anti-cancer drugs or an anti-cancer drug-carrying particle mixture of two types of particles with a size of 10–1000 nm and with a size of 1–1000 μm, the polymer according to the present invention is converted into a hard gel in situ at the physiological condition (e. g., temperature) of the cancer to prevent the drugs from being diffused into other sites as well as from causing various side effects thereon. Additionally, the present invention can take advantage of physiological properties characteristic of cancer cells. For example, because cancer cells are of about pH 6.8, which is known to be lower than that of normal cells, the present invention can utilize a liquefied embolic material which is coagulated at the pH and temperature around caner cell loci, in delivering anti-cancer drug so as to prevent the diffusion of the drugs into other sites. Accordingly, the liquefied embolic material of the present invention can be applied for anti-cancer drug delivery systems.

DETAILED DESCRIPTION OF THE INVENTION

Figure 1:
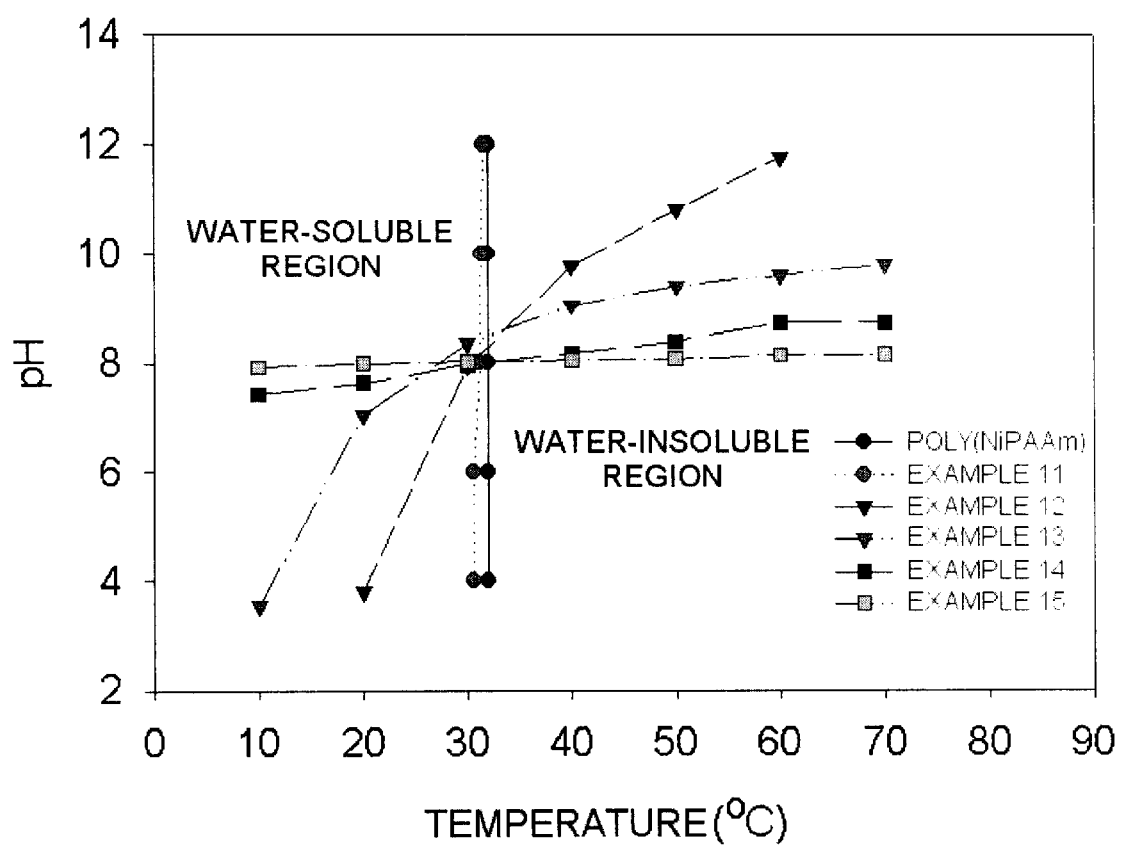
FIG. 1 is a diagram showing the change of water-soluble/water-insoluble regions of poly(NiPAAm-co-SA) according to temperature and pH (ionic strength 0.15, conc. 0.5 wt %).

Based on N-isopropylacrylamide (hereinafter referred to as "NiPAAm"), which is sensitive to temperature, the embolic material of the present invention is a polymer copolymerized with ionic strength- or pH-sensitive monomers.

Preferably, the embolic material of the present invention consists of about 80–99% by mole of NiPAAm and 1–20% by mole of an ionic strength- or pH-sensitive monomer. The constituent monomers are copolymerized to a molecular weight ranging from 500,000 to 5,000,000. This polymer takes a liquid phase in a certain temperature range, but shows phase transition at a critical temperature.

NiPAAm is representative of the monomers which are presently used in temperature-sensitive polymers, copolymers or hydrogels. In the presence of water, NiPAAm homopolymers (hereinafter referred to as "poly(NiPAAm)" is coagulated or subject to in a shrunken state at a low critical solution temperature (LSCT) or higher, that is, 30–32° C. or higher, while remaining dissolved at lower than LSCT owing to predominant hydrogen bonds with water. By taking advantage of this phase transition property, an aqueous NiPAAm solution has been used as an embolic material. When an aqueous solution of poly(NiPAAm) is injected through a catheter to the human body after being solubilized at low temperatures, the sol phase of the polymer is converted into a solid phase within the human body, embolizing the blood vessel. However, if used alone, poly(NiPAAm) is apt to undergo a phase transition into a coagulation within the inserted catheter which has been pre-heated in the human body, thereby clogging the catheter. Further, because the conversion of this homopolymer from hydrophilicity to hydrophobicity and vice versa takes place rapidly, the temperature range in which the homopolymer undergoes phase transition is very narrow: rather than gel, coagulates or shrunken hydrogel is formed, none of which perform complete embolization.

To avoid these problems, the phase transition temperature at which to form gel, can be made to vary with ionic strength or pH in accordance with the present invention. That is, the copolymer of the present invention has a variable LCST which is dependent on ionic strength or pH. Therefore, when being injected through a catheter, a sol phase of the copolymer of the present invention is not gelled within the catheter. Further, the ionic strength- or pH-dependency of the LCST allows the length of time taken for gelling in the blood vessel of a living body to be controlled within a wide range, bringing about a result of complete embolization.

Examples of the ionic strength-sensitive monomers useful in preparing the copolymer of the present invention include acrylic acid, vinylimidazole, N-acryloyl-histidine, N-acryloyl-histamine, urocanic acid, 2-(1-imidazole) ethylmethacrylate, 4-vinylimidazole, and quarternized vinylimidazole.

As for pH-sensitive monomers useful in the present invention, they are exemplified by sulfone amides, such as sulfapyridine, sulfamethoxypyridazine, sulfizomidine, sulfamethazine, sulfadiazine and sulfamethyzol, carboxyl-containing monomers such as methacrylic acid, and amines such as (N,N-dimethylamino)ethyl methacrylate.

Following are representative examples of the temperature-, and ion- or pH-sensitive polymers of the present invention and their properties.

Poly(N-isopropylacrylamide/acrylic acid) (hereinafter referred to as "Poly(NiPAAm-co-AAc)")
copolymerized with N-isopropylacrylamide and acrylic acid and sensitive to temperature and ionic strength.

Poly(N-isopropylacrylamide/acrylic acid/sodium acrylate) (hereinafter referred to as "Poly(NiPAAm-co-Aac-co-SAA)")
able to be prepared by partially replacing the acrylic acid moiety with sodium and once solidified, the gel of this polymer is not converted into a shrunken form.

Poly(N-isoproylacrylamide/vinylimidazole) (hereinafter referred to as "Poly(NiPAAm-co-VI)")
copolymerized with N-isoprpoylacrylamide and vinylimidazole and sensitive to temperature and ionic strength, like poly(NiPAAm-co-Aac).

Poly(N-isopropylacrylamide/sulfonamide) (hereinafter referred to as "Poly(NiPAAm-co-SA)")
copolymerized with N-isoproylacrylamide and sulfonamide and sensitive to temperature and pH.

The above copolymers are summarized in Table 1, below, along with their properties.

TABLE 1

| Polymer Abbreviation | Monomer 1 | Monomer 2 | Characteristic |
|---|---|---|---|
| Poly(NiPAAm-co-AAc) | N-Isopropylacrylamide | Acrylic acid | Sensitive to temp. & ionic strength |
| Poly(NiPAAm-co-AAc-co-SAA) | N-Isopropylacrylamide | Acrylic acid (partially substituted with Na) | Even at high temp., fixed gel is not converted into shrunken gel |
| Poly(NiPAAm-co-VI) | N-Isopropylacrylamide | Vinylimidazole | Sensitive to temp. & ionic strength |
| Poly(NiPAAm-co-SA) | N-Isopropylacrylamide | Sulfonamide | Sensitive to temp. & pH |

In the presence of water, the copolymers of the present invention exist in four apparent phases: a clean solution phase, an opaque solution phase, a stable gel phase and a shrunken state. The term "phase transition temperature" as used herein, unless otherwise stated, means a temperature or a temperature range at which the opaque solution phase of a copolymer is converted into a stable gel phase. As a rule, the phase transition temperature from sol to gel is determined as the temperature when the gel phase is maintained for 1 min after the vial is turned upside down.

The phase transition from sol phase to gel phase of the copolymers according to the present invention takes place without temperature delay nor solvent release. Hence, even when being added with any solvent, the gel, once formed, is not dissolved nor absorbs the solvent, but remains unchanged in the form.

For Poly(NiPAAm-co-Aac) and Poly(NiPAAm-co-VI), both being sensitive to ionic strength, the temperatures at which they show phase transition from sol to gel increase with a decrease in ionic strength. Thus, after being injected through a catheter into dysfunctional blood vessels, the solutions obtained by dissolving the copolymers of the present invention at an ionic strength less than 0.15 (ionic strength of human fluid) are maintained in a sol phase within the catheter and do not transform into a gel phase until they encounter blood.

The reason why the phase transition temperatures of the copolymers are higher at lower ionic strength is as follows.

At a low ionic strength, acrylic acid and vinyl imidazole moieties contained in the copolymers show higher solubility than at a high ionic strength. Also, because the probability that the water molecules associated with the polymers via hydrogen bonds are separated from the polymers to solubilize ions (that is, salting out effect) is lower at lower ionic strengths, the polymers are of greater hydrophilicity. Thus, these copolymers are gelled at low ionic strengths mostly by the influence of the isopolypropylacrylamide moiety. As the temperature increases, the copolymers become more hydrophilic than poly(NiPAAm), so that they require a larger number of hydrophobic groups for phase transition. That is, the copolymers undergo phase transition at relatively high temperatures at which hydrophobic groups are generated in greater quantities. On the other hand, where the ionic strength is relatively strong, the acrylic acid and vinyl imidazole moieties of the copolymers turn hydrophobic. Phase transition occurs when even a small quantity of hydrophobic groups are formed.

With regard to poly(NiPAAm-co-VI), its opaque solution is maintained at up to 60° C. in the absence of ionic strength, but starts to undergo gelling from an ionic strength of 0.02.

In contrast to poly(NiPAAm-co-Aac), poly(NiPAAm-co-VI) maintains an opaque solution phase in a very small range of temperature. Particularly at an ionic strength of 0.15, an opaque solution phase of poly(NiPAAm-co-VI) appears only at around 32° C.

Turning to poly(NiPAAm-co-SA), a pH-sensitive polymer, its sulfonamide moieties are ionized at a certain pH or higher, making the polymer hydrophilic. On the other hand, the sulfonamide moieties remain neutral at less than the critical pH, so that the polymer shows hydrophobicity. Therefore, the phase transition temperature of the pH-sensitive copolymer increases with an increase of pH. Advantage is therefore taken of this characteristic in applying the pH-sensitive copolymer for use in blood vessels. In this regard, the pH-sensitive copolymer is dissolved at higher than pH 7.4 (human blood pH) and injected through a catheter into a dysfunctional blood vessel. While maintaining its sol phase within the catheter, the pH-sensitive copolymer is coagulated at the location where it encounters blood.

At present, sulfonamides are mostly used as antibacterial agents or chelating agents,. Thus far, there have been found or synthesized 15,000 derivatives of sulfonamide with different pKa values. In particular, because their pKa values are near pH 7.4 (the physiological pH), sulfonamide derivatives can be far more useful than other pH-sensitive materials. When sulfonamide is copolymerized with N-isopropylacrylamide, the resulting polymer is gelled in a wider range of temperature at higher pH. That is, the temperature range in which copolymers of sulfonamide and N-isopropylacrylamide are gelled widens as they are subjected to higher pH. For instance, the gelling of the copolymers takes place in the temperature range of 29–34° C. at pH 7.3 and in the temperature range of 32–52° C. at pH 7.8.

To be useful as embolic materials, the copolymers must have a large temperature range in which their gelling takes place. It is advantageous that the copolymers do not undergo the phase transition from a stable gel phase to a shrunken state. In experiments conducted by the present inventors, it was revealed that, when temperature is elevated to a certain point, deionization occurs on the carboxyl group of the AAc moiety of poly(NiPAAm-co-AAc), giving the copolymer hydrophobicity. As the copolymer turns hydrophobic, an upset is caused to the hydrophilicity/hydrophobicity balance on which a stable state of the gel is based, finally causing the stable gel to take on a shrunken state. Based on this experimental data, poly(NiPAAm-co-AAc-co-SAA) was planned. Its preparation may be achieved by subjecting poly(NiPPAm-co-AAc) to acid-base reaction in the presence of sodium hydroxide (NaOH).

As an embolic material, the liquefied copolymers are required to have a gelling temperature of 37° C. or higher at an ionic strength less than 0.15 and a gelling temperature of 32–36° C. at an ionic strength of 0.15.

Over other ionic strength- or pH-sensitive monomers, the monomer N-isopropylacrylamide is dominant in the copolymers of the present invention. Preferably, the portion of N-isopropylacrylamide amounts to 80–90% by mole in a copolymer.

With reference to FIG. 1, there are shown temperature- and pH-dependent changes of water-soluble/water-insoluble ranges of copolymers according to N-isproylacrylamide proportions. As apparent from this figure, the copolymers increase in temperature sensitivity with an increase in N-isopropylacrylamide content while increasing in pH sensitivity with an increase in sulfonamide content.

For use in embolization, the sol phase of the copolymers according to the present invention must have a viscosity high enough to withstand blood flow and low enough to be handled with ease. Preferably, the copolymers of the present invention range from 500,000 to 5,000,000 in molecular weight. For example, if the molecular weight of the copolymers is below 500,000, the sol phase thereof is too low in viscosity to induce gel-formation at a desired location because it is easily dispersed by blood flow. On the other hand, if a copolymer with a molecular weight of more than 5,000,000 is used, the sol phase cannot be handled easily owing to its too high viscosity.

Also, the present invention pertains to a pharmaceutical embolic composition comprising the liquefied embolic material at an amount of 3–20% by weight and, finally to embolotherapy using such a pharmaceutical embolic composition. To stabilize the gel, the pharmaceutical embolic composition may further comprise natural polysaccharides at an amount of 0.1–10% by weight.

The most characteristic feature of the present invention resides in that the liquefied embolic material according to the present invention is solidified, e. g., gelled under the physiological conditions of the body temperature (37° C.) and ionic strength (0.15) or pH (7.4). The embolic material of the present invention is dissolved at higher than pH 7.4 or at an ionic strength of lower than 0.15 and the sol phase of the embolic material is injected through a catheter into a dysfunctional blood vessel. While remaining dissolved within the catheter, the embolic material is coagulated or gelled at a location where it encounters blood. Therefore, the embolic material can be successfully used in embolotherapy. If the injection solution containing the embolic material is greatly different from blood or body fluid in its composition, including ionic strength and pH, it may damage the body. Thus, the injection solution preferably ranges from 0 to 0.14 in ionic strength and from 7.6 to 7.9 in pH.

Another factor determining phase transition temperatures of the copolymers is their concentrations. At high concentrations, the accessibility of water molecules to the copolymers is poorer while the hydrophobic interaction between the isopropyl groups is greater. Thus, water molecules surrounding the copolymers decrease in activity. As for hydrogen bonding and van der Waals attraction, which both have important influence on hydrophobic interaction whether positively or negatively, their strengths are inversely proportional to the distance between two respective points. Therefore, the hydrophobic interaction is closely connected to the concentration.

To facilitate the embolotherapy using the embolic material of the present invention, the sol phase of the copolymers must have such a concentration that it undergoes phase transition in the temperature range of 30–35° C. at an ionic strength of 0.15, forms a stable gel at 37° C., and does not exhibit hysteresis even after the temperature is increased to 43° C. and decreased. Preferably, the gel, once formed, does not undergo phase transition to a shrunken state. The higher the temperature at which the phase transition into a shrunken state occurs, the better. Higher temperatures of the phase transition into a shrunken state indicate that the gel is more stable. The copolymers of the present invention can endure at as high as 80° C. without the phase transition from stable gel state into a shrunken gel state.

In accordance with the present invention, diverse copolymers suitable for use in embolization for treatment of various lesions can be synthesized by changing proportions of monomers and/or through different polymerization processes. For instance, it is preferred to use a sol phase containing a copolymer of isopropylacrylamide and acrylic acid at a concentration of 7% where blood flow is rapid. On the other hand, at loci of relatively slow blood flow, copolymers consisting of isopropylacrylamide and vinylimidazole or sulfonamide are advantageous in terms of injection convenience.

A better understanding of the present invention may be obtained in light of the following examples which are set forth to illustrate, but are not to be construed to limit the present invention.

EXAMPLE 1

Synthesis of Poly(NiPAAm-co-AAc)

A copolymer containing acrylic acid monomers at an amount of 2.0% by mole based on total mole of N-isopropylacrylamide was synthesized as follows. Prior to polymerization, the reactant monomers were made competent for reaction by bubbling with dry nitrogen gas for 30 min followed by deaerating for an additional 30 min. The competent reactant monomers were polymerized at 60° C. for 16 hours in the presence of azobisisobutyronitrile (AIBN) in benzene. This solvent was used at an amount of 10% by weight based on the total weight of the monomers used while the concentration of the initiator was $7 \times 10^{-3}$ mol/mol. The precipitate thus formed was dissolved in acetone/methanol (90/10 v/v), after which the solution was added to diethyl ether to form a precipitate. The resulting solution was dried for 3 days under vacuum and the residue was dialyzed against a semi-permeable membrane (cutoff 15,000) in distilled water for one week to remove unreacted monomers. Freeze-drying the dialysate gave the title polymer.

EXAMPLE 2

Synthesis of Poly(NiPAAm-co-AAc)

The same procedure as in Example 1 was repeated with an exception of using a different molar ratio of isopropylacrylamide to acrylic acid. The molar ratios of isopropylacrylamide to acrylic acid used are given in Table 2, below.

TABLE 2

Molar Ratios of Constituent Monomers in Poly(NiPAAm-Co-AAc)

| Example No. | NiPAAm Mole | AAc Mole |
|---|---|---|
| 1 | 98 | 2 |
| 2 | 95 | 5 |

EXAMPLE 3

Synthesis of Poly(NiPAAm-co-AAc-co-SAA)

In deionized water, the copolymer prepared in Example 1 was dissolved at an amount of 5% by weight and added with sodium hydroxide at an equal mole number to that of the acrylic acid moieties contained in the copolymer, followed by reaction at room temperature for 24 hours. The reaction solution was allowed to precipitate in diethyl ether, after which 3 days of vacuum drying gave the title compound.

EXAMPLES 4–7

Synthesis of Poly(NiPAAm-co-AAc-co-SAA)

A series of poly(NiPAAm-co-AAc-co-SAA) were prepared in a. manner similar to that of Example 3, except that the molar ratios of the AAc moieties of the polymers to NaOH were used as shown in Table 3, below.

TABLE 3

Composition of Poly(NiPAAm-co-AAc-co-SAA)

| Example No. | AAc Mole in Poly(NiPAAm-co-AAc) | NaOH Mole used |
|---|---|---|
| 3 | 2 | 2 |
| 4 | 2 | 1 |
| 5 | 2 | 0.66 |
| 6 | 2 | 0.50 |
| 7 | 2 | 0.25 |

EXAMPLE 8

Synthesis of Poly(NiPAAm-co-VI)

A copolymer containing vinyl imidazole at an amount of 2.0% by mole based on total moles of N-isopropylacrylamide was synthesized as follows. Prior to polymerization, the reactant monomers were made competent for reaction by bubbling with dry nitrogen gas for 30 min followed by deaerating for an additional 30 min. The competent reactant monomers were polymerized at 60° C. for 16 hours in the presence of azobisisobutyronitrile (AIBN) in benzene. This solvent was used at an amount of 10% by weight based on the total weight of the monomers used while the concentration of the initiator was $7 \times 10^{-3}$ mol/mol. The precipitate thus formed was dissolved in acetone/methanol (90/10 v/v) with heating, after which the solution was added to diethyl ether to form a precipitate, and dried for 3 days under vacuum. Afterwards, the residue was dialyzed against a semi-permeable membrane (cutoff 15,000) in distilled water for one week to remove unreacted monomers. Freeze-drying the dialysate gave the title polymer.

EXAMPLE 9

Synthesis of Poly(NiPAAm-co-VI)

The same procedure as in Example 1 was repeated with the exception of using a different molar ratio of isopropylacrylamide to vinyl imidazole. The molar ratios of isopropylacrylamide to vinyl imidazole used are given in Table 4, below.

TABLE 4

Molar Ratios of Constituent Monomers in Poly(NiPAAm-co-VI)

| Example No. | NiPAAm Mole | VI Mole |
|---|---|---|
| 8 | 98 | 2 |
| 9 | 95 | 5 |

EXAMPLE 10

Synthesis of Sulfonamide Monomer with Double Bond

After being dissolved in 40–60 ml of a co-solvent of water/acetone, 10 mmoles of sulfonamide (sulfamethoxypyridazine) and 10 mmoles of methacryloyl chloride were allowed to vigorously react at 10° C. for 24 hours, along with 10 mmoles of NaOH, to obtain a sulfonamide monomer with a double bond as a precipitate. It was filtered and dried at 25° C. for 2 days under vacuum.

EXAMPLE 11

Synthesis of Poly(NiPPAm-co-SA)

A mixture of isopropylacrylamide and a sulfonamide monomer in the molar ratio of 97.5:2.5 was dissolved at an amount of 50 w/v in dimethylsulfoxide (DMSO) and allowed to polymerize in the presence of AIBN (0.2 mole %). Prior to the polymerization, the reactant monomers were made competent for reaction by bubbling with dry nitrogen gas for 30 min followed by deaerating for an additional 30 min. The polymerization was conducted at 65° C. for 24 hours. The reaction solution was dialyzed against a dialysis membrane (cutoff 2,500) for one week. The above procedure was repeated 10 times at different pH values.

EXAMPLES 12 TO 15

Synthesis of Poly(NiPAAm-co-SA)

A series of poly(NiPAAm-co-SA) copolymers were prepared in a manner similar to that of Example 11, except that the molar ratios of isoproylacrylamide to sulfonamide were used as shown in Table 5, below.

TABLE 5

Composition of Poly(NiPAAm-co-SA)

| Example No. | NiPAAm Mole | SA mole |
| --- | --- | --- |
| 11 | 97.5 | 2.5 |
| 12 | 95 | 5 |
| 13 | 90 | 10 |
| 14 | 85 | 15 |
| 15 | 80 | 20 |

TEST EXAMPLE 1

Phase Transition of Poly(NiPPAm-co-AAc) at Various Ionic Strengths

It was observed that the two types of poly(NiPAAm-co-AAc) copolymers prepared in Examples 1 and 2 varied in phase transition temperature, depending on ionic strength. For measuring their phase transition temperatures, each of 5 wt % aqueous solutions of the copolymers were placed in a vial and their temperatures were elevated by 0.5° C. per 5 hours in an incubator. The phase transition from a transparent solution to an opaque solution was determined as a 50% reduction in light transmittance. That is, the temperature at which the light transmittance of the starting solution was reduced by 50% was defined as the phase transition temperature from transparent to opaque. The phase-transition temperature from sol to gel was determined as the temperature at which the gel phase was maintained as is for 1 min after the vial was turned upside down.

Phase transition temperatures of the copolymers synthesized in Example 1 were measured at various ionic strengths and the results are given Table 6, below.

TABLE 6

Phase Transition Temp. of 5 wt % Poly(NiPAAm-co-AAc) (Exmp. 1)

| | Phase Transition Temperature (° C.) | | |
| --- | --- | --- | --- |
| Ionic Strength | Clear → Opaque | Opaque → Gel | Gel → Shrunken |
| 0 | 32 | 36 | 45 |
| 0.15 | 30 | 33 | 42 |

Similar results to those of Table 6 were observed from a 5 wt % solution of the poly(NiPPAm-co-AAc) copolymer synthesized in Example 2.

TEST EXAMPLE 2

Phase Transition of Poly(NiPAAm-co-AAc) at Various Concentrations

Examination was made of whether the phase transition temperatures of solutions of the copolymer were dependent on their concentrations or not. The data obtained from the examination showed that the concentration influenced the phase transition temperatures. Particularly, the phase transition from sol to gel was more greatly affected than any other phase transition. In detail, at 37° C., aqueous solutions of the copolymer synthesized in Example 1 were gelled if their concentration was 3 wt % or higher. However, very unstable gel was formed from 3–4 wt % aqueous solutions. Solutions with concentration of 5 wt % or higher were transformed into stable gel at 37° C. and did not exhibit hysteresis even after the temperature was increased to 43° C. and decreased.

Phase transition temperatures of the copolymer synthesized in Example 1 were measured at various concentrations thereof and the results are given in Table 7, below.

TABLE 7

Change of Phase Transition Temperature of Poly(NiPAAm-co-AAc) (Example 1) According to Concentration (ionic strength 0.15)

| Conc. | Phase Transition Temperature (° C.) | | |
| --- | --- | --- | --- |
| Wt % | Clear → Opaque | Opaque → Gel | Gel → Shrunken |
| 3 | 32 | 37 | 41 |
| 4 | 32 | 35 | 42 |
| 5 | 30 | 33 | 42 |
| 6 | 30 | 32 | 43 |
| 7 | 29 | 31 | 43 |
| 8 | 29 | 31 | 44 |
| 9 | 29 | 30 | 44 |
| 10 | 29 | 30 | 45 |

TEST EXAMPLE 3

Analysis of Gelation of Poly(NiPAAm-co-AAc) Using Light Scattering Spectroscopy The gelation of poly(NiPAAm-co-AAc) was analyzed for dependence on ionic strength by use of light scattering spectroscopy. In this regard, an observation was made of the change in the particle size of poly(NiPAAm-co-AAc) in a 5.0 wt % solution with an ionic strength of 0 or 0.15 while the temperature was increased.

At an ionic strength of 0, the particle size was observed to start to increase at 30° C. and continued to increase to as large as about 2,500 nm when the temperature was elevated to 33° C. From this temperature to 35° C., the particle size was measured to be as small as 200 nm. However, while the temperature was further elevated to 38° C., the particles were found to resume expansion and finally increased to the largest size of 8,700 nm. The reason for the increase in particle size at 33° C. was that the poly(NiPAAm-co-AAc) underwent the phase transition from a transparent solution to an opaque solution at 29° C. to form fine particles which then aggregated into macro particles to form a macro structure gel. The small particle size measured in the temperature range of from 33 to 35° C. was believed to result from the inability of the light scattering device to measure particle sizes larger than the 2,500 nm. The greatest particle size at 38° C. was, to our knowledge, attributed to the fact that the gel of the copolymer entered into a shrunken state in which the hydrophobic groups interacted themselves to form large aggregates.

Under the condition of an ionic strength of 0.15, the particle size started to increase when the temperature was elevated to 30° C. and continued to increase until 33° C., as in conditions of the absence of ionic strength. However, the increase in particle size was limited only to about 250 nm which was far less than 2,500 nm, the particle size at an ionic strength of 0. The formation of small particles indicates the gelation resulting from hydrophobic bonds that the poly (NiPAAm) itself exhibits in the poly(NiPAAm-co-AAc). That is, when reaction was allowed to occur between isopropylacrylamide monomers and acrylic acid monomers for formation of copolymers, acrylic acid monomers are self-polymerized in advance, owing to their greater activity than that of isopropylamide monomers, so that the poly (NiPAAm-co-AAc) has stretches which consist only of isopropylacrylamide, that is, poly(NiPAAm). When being heated to 43° C., the particles increased in size to as large as 10,000 nm and, above this temperature, was measured to be reduced in size. This was believed to because the sensitivity of the polymerized acrylic acid to ionic strength has influence on the conversion into a shrunken state of the gel.

TEST EXAMPLE 4

Phase Transition of Poly(NiPAAm-co-AAc-co-SAA)

Phase transition characteristics of the copolymers prepared in Examples 3 to 7 were measured and the results are given in Table 8, below.

As apparent from Table 8, the copolymers, which had 0.25 moles or greater of.NaOH, did not undergo phase transition from stable gel to a shrunken state, demonstrating its high stability.

TABLE 8

Change in Phase Transition Temperature of Poly(NiPAAm-co-AAc-co-SAA) According to NaOH Content (5 wt %, ionic strength 0)

| Example No. | Phase Transition Temperature (° C.) | | |
|---|---|---|---|
| | Clear → Opaque | Opaque → Gel | Gel → Shrunken |
| 3 | 34 | 41 | No transition |
| 4 | 33 | 37 | No transition |
| 5 | 32 | 36 | No transition |
| 6 | 32 | 36 | No transition |
| 7 | 32 | 35 | No transition |

TEST EXAMPLE 5

Gelation of Poly(NiPAAm-co-VI) According to Ionic strength

Phase transition temperatures of 5 wt % solutions of the poly(NiPAAm-co-VI) prepared in Examples 8 and 9 were measured while varying ionic strength. The results are given in Tables 9 and 10, below.

TABLE 9

Phase Transition Temperature of 5 wt % Solution of Poly(NiPAAm-co-VI) (Example 8)

| Ionic Strength | Phase Transition Temperature (° C.) | | |
|---|---|---|---|
| | Clear → Opaque | Opaque → Gel | Gel → Shrunken |
| 0 | 33 | 75 | No transition |
| 0.03 | 32 | 34 | 45 |

TABLE 9-continued

Phase Transition Temperature of 5 wt % Solution of Poly(NiPAAm-co-VI) (Example 8)

| Ionic Strength | Phase Transition Temperature (° C.) | | |
|---|---|---|---|
| | Clear → Opaque | Opaque → Gel | Gel → Shrunken |
| 0.05 | 32 | 33 | 70 |
| 0.10 | 31 | 33 | 37 |
| 0.15 | 31 | 32 | 35 |
| 0.30 | 30 | 31 | 45 |
| 0.40 | 29 | 30 | 33 |

As seen in Table 9, the poly(NiPAAm-co-VI) did not show the phase transition to gel until 75° C. nor to shrunken gel even at higher temperature when it was subjected to an ionic strength of zero. This indicates that the phase transition of the copolymer is not dependent on temperature alone. In practice, when the copolymer is injected through a catheter into the body, it does not clog the catheter due to temperature changes. The temperatures of phase transition to gel and a shrunken state are steadily decreased with an increase in ionic strength. At physiological conditions of ionic strength (0.15) and temperature (37° C.), gelation suitable for application for embolization in the body took place.

TABLE 10

Phase Transition Temperature of 5 wt % Poly(NiPAAm-co-VI) (Example 9)

| Ionic Strength | Phase Transition Temperature (° C.) | | |
|---|---|---|---|
| | Clear → Opaque | Opaque → Gel | Gel → Shrunken |
| 0 | 35 | 65 | No transition |
| 0.03 | 33.5 | 35 | 38 |
| 0.05 | 33 | 34 | 44 |
| 0.10 | 32 | 33 | 55 |
| 0.15 | 32 | 33 | 56 |
| 0.20 | 31 | 32 | 55 |
| 0.30 | 30 | 31 | 42 |
| 0.4. | 29 | 30 | 32 |

Like the solution of the copolymer prepared in Example 8, the 5 wt % solution of the poly(NiPAAm-co-VI) prepared in Example 9 was not converted to any other phase, but onlt to an opaque solution at an ionic strength of zero. The temperature at which stable gel was formed was successively decreased with an increase in ionic strength. Under the physiological conditions of ionic strength (0.15) and temperature (37° C.), the solution underwent phase transition to a stable gel suitable for use for embolization.

TEST EXAMPLE 6

Gelation of Poly(NiPAAm-co-VI) According to Concentration

Examination was made of the dependence of phase transition temperature of the copolymer on its concentration. In this regard, at a constant ionic strength (0.15), gelation of aqueous solutions which contained two types of poly (NiPAAm-co-VI), prepared in Examples 8 and 9, respectively, at amounts of 3–10% by weight, was observed.

For the copolymer of Example 8, a gelation range of 32–37° C. was measured at a concentration of 3–6% by weight. Solutions with a concentration of 7% by weight or higher underwent phase transition to gel at 30–35° C.

On the other hand, the solutions of the copolymer prepared in Example 9 started to gel at about 32–33° C. irrespective of their concentrations. That is, despite different concentrations, the solutions of this copolymer were converted to gel within a very narrow temperature range. The phase transition of gelation to stable gel and to a shrunken state took place in the temperature range of 33–42° C. for a 3 wt % solution of the copolymer of Example 9. The temperature range for gelation was found to widen with concentration to a certain extent. A wide gelation range of from 33 to 70° C. was detected in a 7 wt % solution, but the gelation ranges narrowed to 32–37° C. for 8–10 wt % solutions.

Details are given in Tables 11 and 12, below.

TABLE 11

Change in Phase Transition Temperature of Poly(NiPAAm-co-VI) (Example 8) According to Concentration (pH 7.4, ionic strength 0.15)

| Conc. | Phase Transition Temp. (° C.) | | |
|---|---|---|---|
| Wt % | Clear → Opaque | Opaque → Gel | Gel → Shrunken |
| 3 | 31 | 32 | 35 |
| 4 | 31 | 32 | 35 |
| 5 | 31 | 32 | 35 |
| 6 | 31.5 | 32 | 35 |
| 7 | 29 | 31 | 35 |
| 8 | 29 | 31 | 35 |
| 9 | 29 | 31 | 35 |
| 10 | 29 | 31 | 36 |

As seen in Table. 11, apparent phase transition of the copolymer of the present invention took place under the physiological pH and ionic strength conditions.

TABLE 12

Change in Phase Transition Temperature of Poly(NiPAAm-co-VI) (Example 8) According to Concentration (pH 7.4, ionic strength 0.15)

| Conc. | Phase Transition Temp. (° C.) | | |
|---|---|---|---|
| Wt % | Clear → Opaque | Opaque → Gel | Gel → Shrunken |
| 3 | 32 | 33 | 42 |
| 4 | 32 | 33 | 49 |
| 5 | 32 | 33 | 47 |
| 6 | 32 | 33 | 41 |
| 7 | 31.5 | 32 | 70 |
| 8 | 31 | 32 | 37 |
| 9 | 31 | 32 | 37 |
| 10 | 31 | 32 | 37 |

Solutions containing the copolymer of Example 9 at various concentrations also underwent phase transition under the physiological pH and ionic strength conditions. Over the concentration range of from 3 to 10 wt %, stable gel was formed. However, if the solutions contain the copolymer at a large amount, they are too viscous to be injected into blood vessels. Preferable is a solution with a concentration of 5–7 wt %.

TEST EXAMPLE 7

Analysis of Gelation of Poly(NiPAAm-co-VI) Using Light Scattering Spectroscopy

The gelation of poly(NiPAAm-co-VI) was analyzed by use of light scattering spectroscopy as in poly(NiPAAm-co-AAc).

With regard to a 0.2 wt % solution of the copolymer prepared in Example 9, its particle size was maintained in the size range of 40–45 nm at an ionic strength of 0 while the temperature was elevated from 25 to 33° C. Above this temperature, the particle size greatly increased, to a size of as large as 68 nm at 37° C. under the same ionic strength condition. Then, this size remained almost unchanged even when the temperature was further elevated to 45° C. Different from that of the poly(NiPAAm-co-AAc), this particle size change behavior of poly(NiPAAm-co-VI) indicates that poly(NiPAAm-co-VI) is not gelled, but exists in the form of particles at an ionic strength of zero.

TEST EXAMPLE 8

Change in Water-Soluble/Water-Insoluble Regions of Poly(NiPAAm-co-SA) According to Temperature and pH Measurement was made of how the water solubility of poly(NiPAAm-co-SA) copolymers were changed with temperature and pH, by taking advantage of the light transmittance of their aqueous solutions. The results are depicted in FIG. 1. An aqueous solution of a polymer was determined as being water-insoluble when its light transmittance was decreased to below 50%. As shown in this figure, whether poly(NiPAAm-co-SA) copolymers are water-soluble or water-insoluble is more decisively determined by pH when the sulfonamide proportion is greater and by temperature when the sulfonamide proportion is smaller.

(alternative), the solubility of poly(NiPAAm-co-SA) copolymers is more highly sensitive to pH when the proportion of SA is low, and more highly sensitive to temperature when the proportion of solfonamide is high.

TEST EXAMPLE 9

Change in Phase Transition Temperature of Poly (NiPAAm-co-SA) (Example 12) According to pH The phase transition temperature of the poly(NiPAAm-co-SA) copolymer prepared in Example 12 was found to highly sensitive to changes in pH values. Under the condition of pH 7.3, the copolymer underwent phase transition from a transparent solution to an opaque solution at 25° C. This phase transition temperature was not greatly changed up to pH 7.8. However, the phase transition of gelation to stable gel and to a shrunken state took place in the temperature ranges of 29–34° C. at pH 7.3, and 32–52° C. at pH 7.8. The results are given in Table 13, below.

TABLE 13

Phase Transition Temperature of Poly(NiPAAm-co-SA) (Example 12) at Various pH Values (ionic strength 0.15)

| pH | Phase Transition Temp. (° C.) | | |
|---|---|---|---|
| | Clear → Opaque | Opaque → Gel | Gel → Shrunken |
| 7.3 | 25 | 29 | 34 |
| 7.4 | 25.5 | 30 | 37 |
| 7.5 | 25.5 | 30.5 | 41 |
| 7.6 | 26 | 32 | 44 |
| 7.7 | 26 | 33 | 47 |
| 7.8 | 26 | 32 | 52 |

TEST EXAMPLE 10

Embolization Test in Animal

In solution of pH 7.4, with an ionic strength of 0.10, the poly(NiPAAm-co-AAc) copolymer prepared in Example 1 was dissolved at amounts of 5 and 10% by weight. The resulting injection solutions were intravenously administered through catheters to five test dogs. When the solutions reached sites of blood flow, different embolization results were obtained according to blood flow speed and solution concentration. Where blood flowed rapidly, it was observed that the 5 wt % solution was not to be gelled, but dispersed because of its low viscosity. In blood vessels through which blood flowed slowly, such as capillary vessels, the 5 wt % solution was coagulated in the form of threads to perform embolization. On the other hand, the 10 wt % solution was observed to form a gel as soon as it made egress from the catheter, irrespective of whether the blood flowed rapidly or slowly. This observation indicates that more viscous solutions are more effective for embolizing blood vessels through which blood flows rapidly.

TEST EXAMPLE 11

Gelation in in vitro Model

In a solution with an ionic strength of zero was dissolved the poly(NiPPAm-co-VI) copolymer prepared in Example 4 at an amount of 5% by weight. Through a catheter 1 m long, the resulting solution was injected to a test solution with the physiological properties of pH 7.4, with an ionic strength of 0.15, maintained at 37° C. No sooner had the solution encountered the artificial blood after flowing through and out of the catheter than the solution was transformed into a gel in situ at the contact site. Also, the gel was observed to expand in a balloon-like fashion.

TEST EXAMPLE 12

Molecular Weight Measurement of Poly(NiPAAm-co-AAc)

Measurement was made of molecular weights of the poly(NiPAAm-co-AAc) copolymers synthesized in Examples 1 and 2 by use of light scattering spectroscopy. In this regard, each of the copolymers was dissolved at four different concentrations (0.1, 0.2, 0.3 and 0.4 w/v) in methanol and filtered through a membrane with a pore size of 0.2 $\mu$m to remove impurities. The injection solution thus obtained were measured for index of refraction. Using an He/Ne laser, a light scattering test was performed on the solutions in the range of 40–140° at 25° C. The poly (NiPAAm-co-AAc) synthesized in Examples 1 and 2 were found to range, in weight average molecular weight, from 1,050 to 1,800,000 as calculated according to the Zimm diagram.

TEST EXAMPLE 13

Molecular Weight Measurement of Poly(NiPAAm-co-VI)

The poly(NiPAAm-co-VI) copolymers synthesized in Examples 8 and 9 were measured for molecular weight in the same manner as in Test Example 10. Their weight average molecular weights were found to fall within the range of 1,000,000 to 1,500,000 as calculated according to the Zimm diagram.

Because of its being converted to gel under a specific set of conditions defined by a temperature parameter and an ionic strength parameter or a pH parameter, the liquefied embolic material according to the present invention is free from clogging catheters by being gelled within catheters, unlike conventional materials sensitive only to temperature. Under the conditions which meet all the requirements for temperature, ionic strength and pH, the liquefied embolic material of the present invention is instantaneously converted into a solid form, thereby preventing itself from being released out of the lesion of interest where it is injected. With these advantages, the embolic material of the present invention is capable of complete embolization of blood vessels of interest.

The embolic material of the present invention is a ready-polymerized polymeric mass which need not be further polymerized and filtered, so that the embolotherapy using the embolic material can avoid the side effects resulting from the polymerization of monomers and the generation of impurities within the human body. Additionally, no organic solvents are used upon the application of the embolic material; thus it can also avoid the side effects attributable to solvent leakage. Further, the embolic material can be applied for the embolization of a broad spectrum of lesions, including solvent-sensitive loci.

By virtue of its non-degradability, the embolic material of the present invention can bring about the effect of preventing the recurrence of blood flow in the embolized blood vessel.

Constituting the embolic material of the present invention, synthetic copolymers can be made to have diverse molecular weights and viscosity properties by changing proportions of monomers and through different polymerization processes: embolic materials can be readily made suitable for use in the embolization of blood vessels of interest.

Further, the embolic material according to the present invention can be transformed to gel which is highly stable. Furthermore, the copolymers according to the present invention exhibit better gel stability when being used in combination with other particulate embolic materials or natural polymers helpful in stabilizing the gel than when being used alone. With such superior gel stability, the copolymers of the present invention find excellent applications in the extracellular matrix for cell culture and drug-delivery systems for cancer therapy.

The present invention has been described in an illustrative manner, and it is to be understood that the terminology used is intended to be in the nature of description rather than of limitation. Many modifications and variations of the present invention are possible in light of the above teachings. Therefore, It is to be understood that within the scope of the appended claims, the invention may be practiced otherwise than as specifically described.

What is claimed is:

1. A liquefied embolic material, consisting essentially of a copolymer in a liquid phase consisting of about 80–99% by mole of N-isopropylacrylamide and 1–20% by mole of an ionic strength-sensitive monomer or pH-sensitive monomer, said copolymer having a molecular weight ranging from 500,000 to 5,000,000, wherein said copolymer undergoes a phase transition to a gel phase subsequent to injection into a living body.

2. The liquefied embolic material as set forth in claim 1, wherein the ionic strength-sensitive monomer is acrylic acid.

3. The liquefied embolic material as set forth in claim 1, wherein the ionic strength-sensitive monomer is vinyl imidazole.

4. The liquefied embolic material as set forth in claim 1, wherein the pH-sentive monomer is a sulfonamide derivative.

5. The liquefied embolic material as set forth in claim 4, wherein the sulfonamide derivative is selected from the group consisting of sulfapyridine, sulfamethoxypyridazine, sulfizomidine, sulfamethazine, sulfadiazine and sulfamethyzol.

6. The liquefied embolic material as set forth in any one of claims 1 to 5, wherein the embolic material does not undergo phase transition from a stable gel to a shrunken state at less than 43° C.

7. The liquefied embolic material as set forth in claim 6, wherein the embolic material does not undergo phase transition from a stable gel to a shrunken state at less than 80° C.

8. The liquefied embolic material as set forth in claim 2, wherein the acrylic acid is partially substituted with NaOH and the copolymer is represented by poly(N-isopropylacrylamide/acrylic acid/sodium acrylate).

9. A pharmaceutical embolic composition, comprising the liquefied embolic material in any one of claims 1 to 5 at an amount of 3–20% and a gel stabilizing material at an amount of 0.1–10%.

10. The pharmaceutical composition as set forth in claim 9, wherein the gel-stabilizing material is a natural polymer or a synthetic polymer.

11. An ant-cancer drug delivery system, comprising the liquefied embolic material in any one of claims 1 to 4 and an anti-cancer drug, characterized in that the anti-cancer drug delivery system is gelled as soon as it is injected to a cancer lesion.

* * * * *